United States Patent [19]

Hüschelrath et al.

[11] Patent Number: 4,750,134

[45] Date of Patent: Jun. 7, 1988

[54] DEVICE FOR THE NON-DESTRUCTIVE TESTING OF FERROMAGNETIC BODIES AND A PROCESS FOR PRODUCING VALUES FOR ADJUSTING THE DEVICE INTO AN INITIAL STATE FOR TESTING DETERMINED BY THE RESPECTIVE TEST SAMPLES

[75] Inventors: Gerhard Hüschelrath, Laufach, Fed. Rep. of Germany; Herbert Diehl, Erlensee, Fed. Rep. of Germany

[73] Assignee: Nukem GmbH, Hanau, Fed. Rep. of Germany

[21] Appl. No.: 806,959

[22] Filed: Dec. 9, 1985

[30] Foreign Application Priority Data

Dec. 21, 1984 [DE] Fed. Rep. of Germany ....... 3446867

[51] Int. Cl.$^4$ ...................... G01N 27/82; G01R 33/12
[52] U.S. Cl. .................... 364/507; 324/228; 324/232; 324/238
[58] Field of Search ............... 364/550–552, 364/507, 512; 324/216, 228, 232, 235, 238, 219–221; 73/618, 622, 623

[56] References Cited

U.S. PATENT DOCUMENTS

| | | | |
|---|---|---|---|
| 4,087,749 | 5/1978 | McCormack | 324/235 |
| 4,439,730 | 3/1984 | Kauffman | 324/232 |
| 4,468,619 | 8/1984 | Reeves | 324/235 |
| 4,538,108 | 8/1985 | Hüschelrath et al. | 324/232 |

OTHER PUBLICATIONS

H. Hepner and H. Stoppe, "Magnetische und magnetinduktive Werkstoffprufung", May 10, 1972, pp. 103–107 and 172, 173.

Primary Examiner—Parshotam S. Lall
Assistant Examiner—Brian M. Mattson
Attorney, Agent, or Firm—Cushman, Darby & Cushman

[57] ABSTRACT

This invention provides for the non-destructive testing of a longitudinally displaceable ferromagnetic body for structural faults. This device sends a stationary magnetic field transversely across the body of the test piece. Changes in this magnetic field, due to structural defects of the test piece, are detected by the magnetic field detectors which are placed on the periphery of the test piece in alignment with the stationary magnetic field. The changes detected by the magnetic field detectors must be processed in order to be useful. This processing requires compensation for the varying strength of the magnetic field at the surface of each different magnetic field detector, compensation for unequal sensitivities of each individual magnetic field detector in detecting structural defects, and also compensating for the tolerances of circuits which are used in the previous compensations.

9 Claims, 4 Drawing Sheets

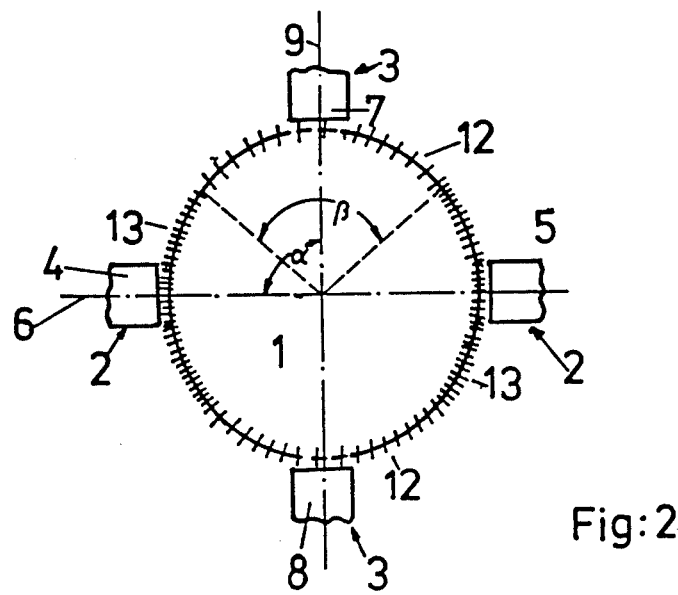
Fig:2
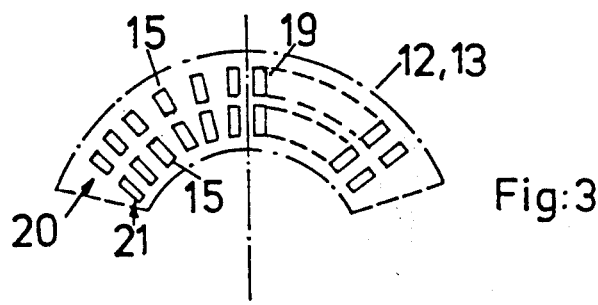
Fig:3
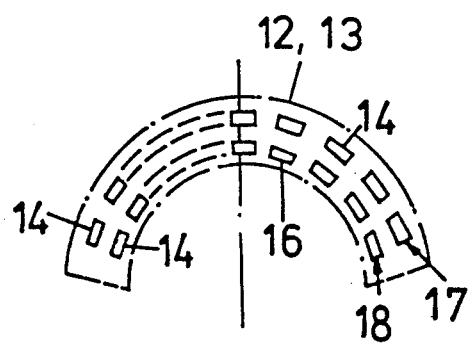
Fig:4

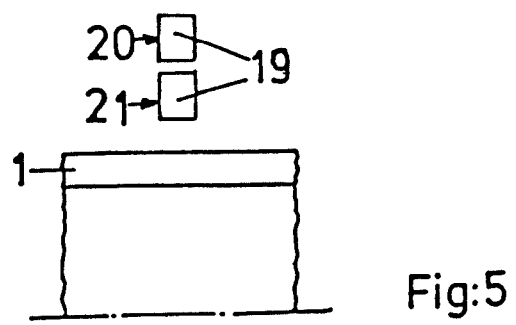
Fig:5
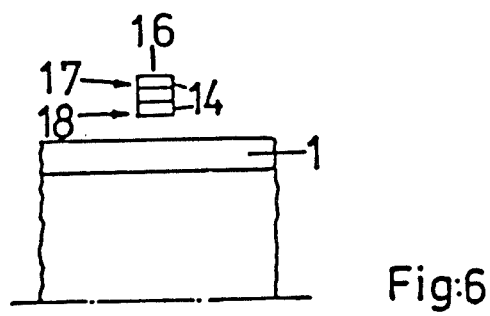
Fig:6
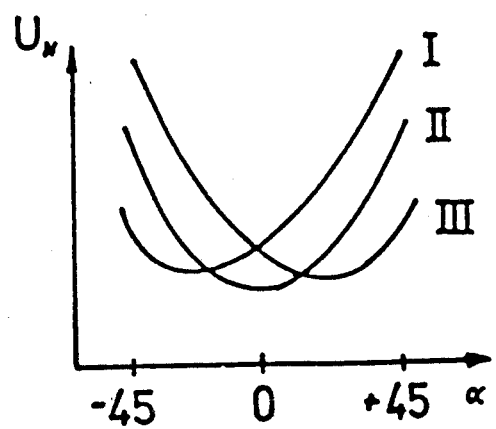
Fig: 7

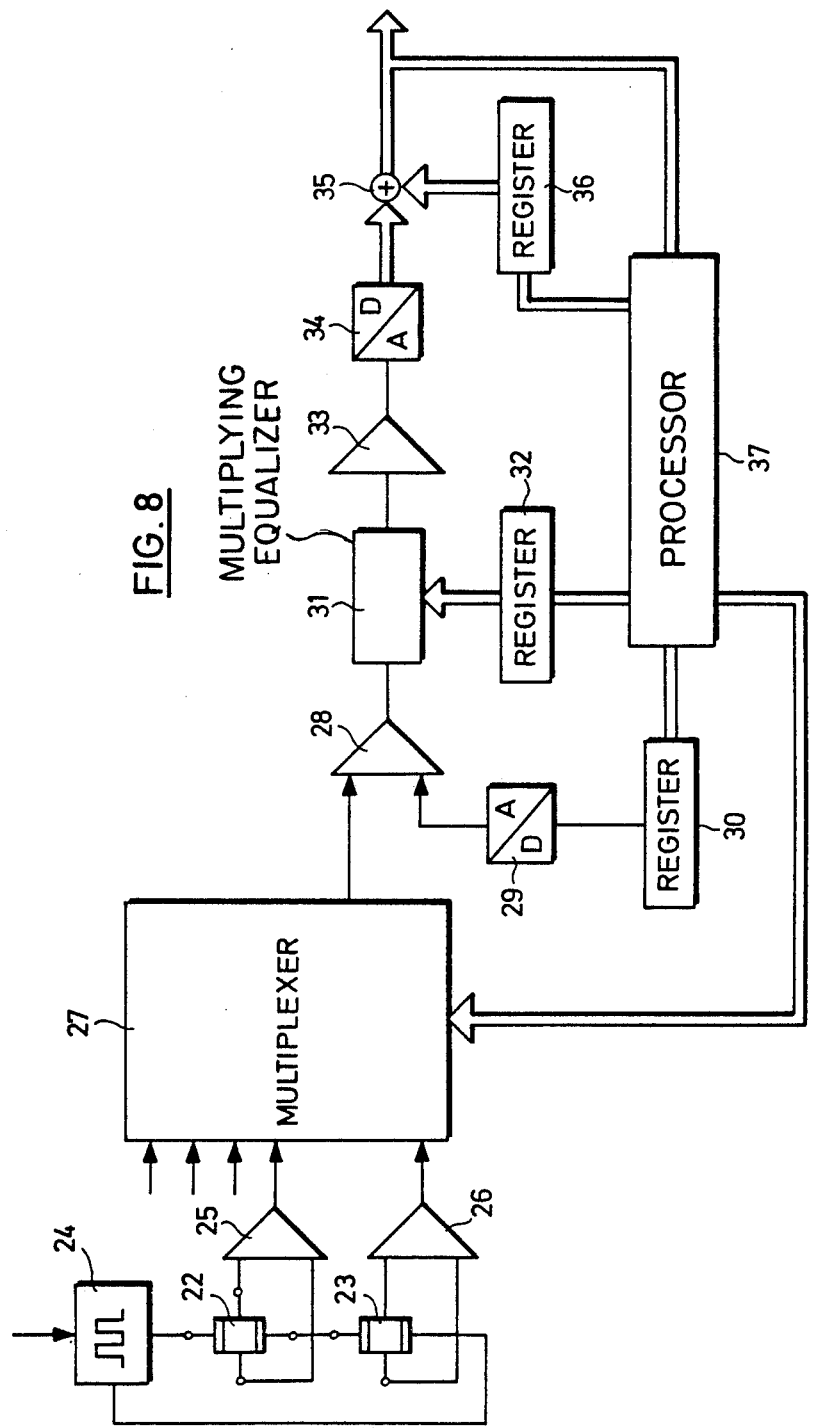

DEVICE FOR THE NON-DESTRUCTIVE TESTING OF FERROMAGNETIC BODIES AND A PROCESS FOR PRODUCING VALUES FOR ADJUSTING THE DEVICE INTO AN INITIAL STATE FOR TESTING DETERMINED BY THE RESPECTIVE TEST SAMPLES

BACKGROUND OF THE INVENTION

This invention relates to a device for non-destructive testing of ferromagnetic bodies and to a process for producing values for adjusting the device into an initial state for testing determined by the respective test samples.

A process is known for the non-destructive testing of longitudinally displaceable ferromagnetic bodies for structural faults by magnetizing the respective bodies, on which at least one stationary magnetic field is directed. Structural faults in the bodies cause changes in the course of the magnetic field which are detected by magnetic field detectors arranged resting on or close to the body surface. The magnetic field detectors are arranged in the space between the poles of the respective magnetic field producer in at least one row along the periphery of the body and vertically to the direction of displacement thereof and are each connected by two electrodes in differential connection to inputs of a multiplexer. At the output of the multiplexer is connected a compensation amplifier which is supplied with compensation values according to which one of the magnetic field detectors is selected. Compensation values are necessary due to the uneven size of the magnetic field on the different magnetic field detectors are compensated (DE-PS 31 32 808).

It is an object of the present invention to improve a device of the above-described type such that despite high dynamics of the output signals of the magnetic field detectors, measuring errors due to the position of the respective magnetic field detector and the spread of the parameters of the magnetic field detectors are substantially reduced.

The invention provides a device for the non-destructive testing of longitudinally displaceable ferromagnetic bodies for structural faults by magnetizing a respective body. Structural faults in the bodies are detected by magnetic field detectors arranged resting on, or close to the body surface in free space between poles of a magnet. They are arranged in at least one row along the periphery of the body, vertically to the direction of displacement thereof, and are each connected to a multiplexer. A compensation amplifier is connected to the output of the multiplexer and is supplied with compensation values which are allocated to the individual magnetic field detectors. An equalizer is connected to the compensation amplifier. This equalizer is supplied with a further input with multiplication coefficients to compensate for unequal sensitivities of the detectors and varying intensities of the magnetic field. An analog-digital converter is connected to the output of the equalizer, to which converter an input of adding device is connected. Compensation values which are inputted through the second input of the adder can be supplied to compensate for tolerances of circuit parts of circuits being arranged before the adding device.

Undesirable influences on the measuring accuracy can be substantially removed. The influences result both from the varying intensity of the magnetic field along the row of magnetic field detectors as well as from the spread of the parameters of the magnetic field detectors. In addition, there are the influences on the measuring accuracy caused by the measured value processing members connected one behind the other, which influences can be likewise substantially compensated.

The multiplying equalizer is preferably an analog multiplier. By means of the analog multiplier, an additional amplification of the signals outputted by the compensation amplifier are achieved. Analog multipliers are commercially cheaply available, such that the circuit arrangement can be produced economically. The amplification by the analog multiplier is moreover high so that an additional amplifier behind the analog multiplier can be dispensed with.

In a preferred embodiment, the registers are connected to a processor or are an integral part of a processor. The compensation values supplied by the processor to the registers can be outputted synchronously to the change-over of the inputs of the multiplexer. The processor can also control the change-over of the multiplexer. The compensation values are recorded in the register according to the respective position of the multiplexer.

A process for producing values for adjusting the device according to the invention into an initial state which is ready to test samples comprises the steps of: using a test sample having no structural faults and measuring the initial values of the compensation amplifier for each of the different magnetic field detectors and recording each of said values as compensation values, then using a test sample which contains test faults of predetermined form and size to obtain the initial values of the multiplication coefficients while utilizing the compensation values established in the previous step and recording the multiplication coefficients obtained, and then obtaining the initial values of the adding device by using the test sample having no structural faults and recording the initial values for each of the magnetic field detectors. For the different types and forms of test samples, a fault-free test sample and a test sample provided with predetermined faults are in each case necessary for adjusting the testing device for testing. When the compensation values allocated to a test sample of particular form and type have been determined and recorded, they can be used again in a later test without the testing device having to be readjusted by means of a fault-free test sample and a test sample provided with faults.

BRIEF DESCRIPTION OF THE DRAWINGS

Further details, characteristics and advantages of the invention will emerge from the following description of one embodiment shown in diagrammatic form.

FIG. 2 shows a front view of the arrangement shown in FIG. 1, FIG. 3 shows a front view of details of the row of magnetic field detectors shown in FIG. 1.

FIG. 4 shows a front view of an embodiment of a row with a different arrangement of the magnetic field detectors, FIG. 5 shows the row shown in FIG. 2 in cross-section, FIG. 6 shows the row shown in FIG. 3 in cross-section, FIG. 7 shows diagrams of the Hall voltages produced by the Hall generators in series according to the position in the series, FIG. 8 shows a block diagram of a device connected to magnetic field detectors for the non-destructive testing of ferromagnetic bodies.

DESCRIPTION OF THE PREFERRED EMBODIMENT

Figure 1:
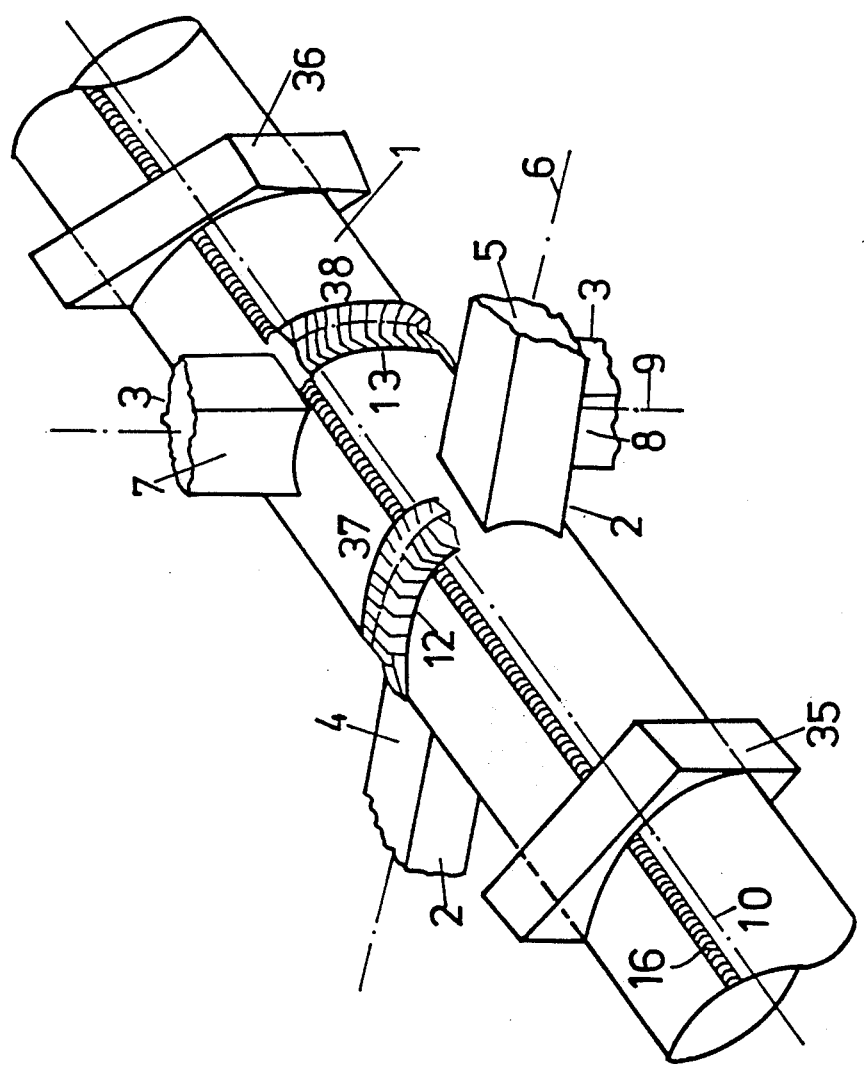
FIG. 1 shows a perspective view of a device for the non-destructive testing of ferromagnetic bodies.

A device for non-destructive testing of ferromagnetic tubes 1, of which one is shown in FIGS. 1 and 2, contains a magnetizing system of two pairs of magnets 2, 3 which are arranged one behind the other in a longitudinal direction of the tube 1. The pair of magnets 2 contains a first magnetic pole shoe 4, the end of which inclined towards the tube is, for example, a magnetic north pole, and a second magnetic pole shoe 5, which on the end inclined towards the tube 1 has a magnetic pole which is opposite to that of the first pole shoe 4. The magnetic pole shoes 4, 5 are arranged along the same central axis 6. The pair of magnets 3 likewise consists of two magnetic pole shoes 7, 8, whereby the pole shoe 7 has a magnetic north pole on its front face inclined towards the tube 1 and the pole shoe 8 has a magnetic south pole on its front face adjacent to the tube 1. The magnetic pole shoes 7, 8 are also arranged along a common central axis 9. Whereas the pairs of magnets 2 and 3 are fixed stationary, the tube 1 is moved during testing between the magnetic pole shoes 4, 5, 7 and 8 in the direction of its longitudinal axis 10. The magnetic fields are directed at the tube 1 by the magnetic pole shoes 4, 5, 7 and 8. The central axes of these magnetic fields in each case correspond with the central axes 6 and 9 of the magnetic pole shoes 4, 5 or 7, 8. The central axes 6 and 9 are inclined towards each other at an angle which corresponds to the quotient of 180° and the number of magnetic fields directed at the tube 1. Since two magnetic fields are directed at the tube 1, the angle is 90°. The lines of the magnetic fields run in the interior of the tube, predominantly in the tube walls. The magnetic fields are so intense that the tube walls are magnetically saturated.

The magnetic resistance is substantially increased by cracks, cavities or holes in the tube walls. Part of the magnetic field does not run over the cracks, cavities or holes, but emanate into the air gap outside the outer or inner tube surface. This part of the magnetic field is detected by magnetic field detectors. The measurement of such a field running outside the tube surface thus indicates a material fault or a structural fault in the walls of the tube 1.

Between the pole shoes 4, 5 or 7, 8 directed at the tube 1 are arranged rows 12 or 13 of magnetic field detectors along the surface of the tube 1. The rows 12, 13 are at a small distance from the surface of the tube 1. In FIGS. 1 and 2, the rows 12 and 13 are arranged close to the outer walls of the tube 1. Rows of magnetic field detectors can also be arranged in the interior of the tube 1, which extend along the inner surface.

The rows 12, 13 detect a test zone in the tube 1 which extends in the direction of axis 10 and has a width which corresponds to the length of the respective row 12 or 13. The rows 12, 13 are arranged stationary as are the pairs of magnets 2, 3. The two rows 12 and the two rows 13 in each case detect two zones on the surface of the tube 1 which each include an angle $\beta$, which is produced from 180° divided by the number of magnetic poles. Each individual row 12, 13 includes at least this angle of 45°. The rows 12, 13 can also be of a longer design such that an angle $\beta$ is produced which is greater than 45°. With the size of the rows 12 and 13 shown in FIGS. 1 and 2, the tube 1 can be tested over the entire periphery.

If a testing apparatus is required with which the tube 1 is to be tested, not over the entire periphery, but over part of the periphery which corresponds, for example, to the width of a weld seam, a row of magnetic field detectors can be provided which only has the width of the desired section of the periphery. The use of only one pair of magnets can be sufficient here. The testing device shown in FIGS. 1 and 2 may be operated such that not the entire periphery but only a section of the periphery is tested. This is explained in more detail below.

Hall generators are provided in the rows 12, 13 as magnetic field detectors, to which pulse sequences are supplied as control currents. The outputs of the Hall generators are provided in time division multiplex and are supplied to an evaluation circuit still to be described below. The inquiry by the time division multiplex of the Hall generators is synchronized by the pulse sequences of the control currents.

In the rows 12, 13 Hall generators 14, 15 can be arranged in varying alignment to the surface of the tube 1. In FIG. 4 and FIG. 6, Hall generators 14 are shown which are aligned with their broad sides 16 aligned with the surface of the tube 1. Two positions 17, 18 of Hall generators are above each other. Which position 17, 18 is used by Hall generators 14 for the fault testing, depends on the nature of the test. The highest sensitivity for fault determination is produced in the differential connection of Hall generators adjacent in the positions 17 and 18.

The Hall generators 15 are arranged in the embodiment shown in FIGS. 3 and 5 with their broad sides 19 vertical to the opposite surface element of the tube 1. The Hall generators 15 are arranged one above the other in two positions 20, 21. The use of the respective position 20, 21 for fault testing is dependent on the selection criteria of the fault just as in the arrangement shown in FIG. 4. The design according to FIG. 3 allows a dense package of Hall generators 15 next to each other. Thus, faults in the structure of the tube 1 can be better localized.

As a result of varying spacings of the Hall generators 14 or 15 arranged in the rows 12, 13 to the magnetic pole shoes 4, 5 or 7, 8, the produced Hall voltages vary. In FIG. 7, the relationship of the Hall voltages $U_H$ of Hall generators arranged in series according to the angle position $\alpha$ is represented. The centre between two magnetic poles 4, 5 or 7, 8 was thereby allocated to the angle 0°. At the positions marked 45°, the upper edges of the magnetic pole shoes 4, 5 or 7, 8 are located. In the vicinity of these magnetic pole shoes, larger Hall voltages $U_H$ occur than at the 0° position. The Hall voltages $U_H$ show a parabolic curve. The curve marked II is produced when the longitudinal axis 10 of the tube 1 runs through the longitudinal axes formed by the pairs of magnets 4, 5 and 7, 8. For tubes displaced eccentrically, the Hall voltage $U_H$ has a different course. The curve I is produced in a position in which the tube 1 is displaced towards the right with its longitudinal axis 10 from the position shown in FIGS. 1 and 2. The curve III of the Hall voltage $U_H$ occurs during displacement of the tube 1 a position lying to the left of the position shown.

In FIG. 8, two Hall generators 22, 23 are shown with their connecting electrodes. The rows 12, 13 of magnetic field detectors shown in FIG. 2 are formed from Hall generators in either the arrangement shown in FIG. 3, which is made up of Hall generators 15 in one configuration or the arrangement shown in FIG. 4, where the Hall generators are in a different configuration. The adjacent pairs of Hall generators 14 and 15 shown in positions 17 and 18 in FIG. 4 or positions 20 and 21 in FIG. 3 correspond to the Hall generators 22 and 23 shown in FIG. 8.

The electrodes for supplying the control current are connected in series in the case of the Hall generators 22, 23. A constant current generator 24 feeds the electrodes the control current. The electrodes for generating the Hall voltage are connected in the case of the hall generators 22, 23 to an input of an amplifier 25, 26.

The constant current generator 24 produces a pulse sequence with a pulse pause to pulse duration ratio of 1:10.

The outputs of the amplifiers 25, 26 are connected to the inputs of a multiplexer 27 which is also connected to the amplifiers fed by the other Hall generators 14 or 15. These amplifiers are not shown in more detail. The multiplexer 27 is connected to an input of a compensation amplifer 28, on which receives from the multiplexer 27 the analog signals generated by the amplifiers 25, 26 or by the other amplifers which are not shown.

The compensation amplifier 28 is a differential amplifier. The second input of the differential amplifier 28 is fed by a digital-analog convertor 29, the digital inputs of which are connected to a first register 30. The output of the compensation amplifier 28 is connected to a multiplying equalizer 31 which is provided with the respective multiplication coefficient via a further register 32. An amplifier 33 is connected to the output of the equalizer 31, to which an amplifier and an analog-digital convertor 34 is connected downstream. The first inputs of an adding device 35 are connected to the output of the analog-digital convertor 34 and the second inputs are connected to an additional register 36. The outputs of the adding device 35 are connected to the inputs of a processor 37 which is connected to the inputs of the register 30, 32 and 36 via outputs. The processor 37 is also connected to the control inputs of the multiplexer 27.

The position influence shown in FIG. 7 of the Hall voltages $U_H$ of the Hall generators must be removed in order to achieve a high measuring accuracy. The processor 37 contains a memory, not shown, in which correction values are stored for the different positions of the Hall generators 14 or 15. The correction values relate both to the arrangement of the tube 1 where the longitudinal axis 10 runs through the longitudinal axes formed by magnet pairs 4, 5 and 7, 8 and to the arrangement where tube 1 is in an eccentric position.

The positioning of the tube 1 is assessed for structural faults by recording a Hall voltage curve as shown in FIG. 7. This Hall voltage curve supplies a compensation value for the position of the respective Hall generators 14 or 15 which is recorded. Before scanning the corresponding Hall generator, the accompanying compensation value is entered in the register 30. The Hall voltages supplied to the compensation amplifer 28 are then corrected by the compensation values from the register 30.

By changing over the output of the multiplexer 27 to another input in each case, the compensation value which is allocated to the Hall generator connected to this input is entered in the register 30.

Since the multiplexer 27 already as a certain amplification, which, for example, lies between 100 and 1000, substantial differences in level occur at the output of the multiplexer in the case of the different Hall generators, which must be reduced in order to reduce measuring faults. The compensation values dependent on the position of the magnetic field probes are supplied to the compensation amplifier 28 via the digital to analog convertor 29. All large indication errors and the residual level can thus be compensated from the magnetic field distribution.

However, in addition to the purely additive deviation values, multiplicative deviation values also occur over the cross sections of the Hall generators. These are produced in that the sensitivity characteristics of the Hall generators are dispersed and that due to the varying field intensity distribution the indication errors are also of varying size. The indication errors increase towards the edge in a parabolic manner. The compensation of these errors takes place via the multiplying equalizer 31. The multiplication coefficients remain probe-dependent in the register 32. Only after this compensation are the signals amplified to the final level by the amplifier 33, before being digitized by an analog-digital convertor 34. Since wider tolerance limits are produced by the processing stages 28, 31, 33, 34 and residual tolerances are further reinforced, the final compensation takes place in the adding device 35. The compensation values are deposited prove-dependent in the register 36.

This compensation in three stages takes place for reasons of dynamics. Since an analog-digital conversion in the required time does not produce the necessary high distribution, interference levels should be suppressed before the actual amplification.

The multiplying equalizer 31 can be an analog multiplier. An analog-digital convertor is therefore to be connected to the register 32. Since such analog multipliers also provide an amplifying function, the amplifier 33 can often be dispensed with. It is also possible to use a multiplying analog-digital convertor as an equalizer 31, having digital multiplying inputs of which are connected to the register 32.

So as to be able to bring the device shown in FIGS. 1 to 6 and 8 into an initial stage for testing which is determined by the respective test samples, the compensation values are initially in the following way.

With a test sample which has no structural faults, and is thus fault-free, the analog compensation values are initially initially determined and stored for each Hall generator.

A second run of a test sample through the above-described device then takes place with a test sample which has structural faults of a known form, size and position in the test sample. This second test run provides fault compensation data, also referred to as multiplication coefficients. The analog compensation values are already supplied to the compensation amplifier 28 for each Hall generator which is selected by multiplexer 27. The multiplication coefficients have to be predetermined to avoid the possibility of giving measurements which indicate that faults which are actually of equal form, size and position are outputted as having a different form, size or position. Also avoided is the possibility of similar outputs for faults of different form, size or position. These multiplication coefficients are stored for each Hall generator.

A third test sample run using a fault-free test sample follows. During this run, the analog compensation values and the multiplication coefficients are already provided and are applied on the compensation amplifier 28 and on the equalizer 31, respectively. Adder quantities determined in the third test run are stored for each Hall generator. These adder quantities are supplied during testing of tubes 1 with unknown faults to the adding device 35 via the register 36 according to the position of the selected Hall generator.

During testing, processor 37 controls which of the predetermined compensation values, multiplication coefficients and adder quantities are supplied to the compensation amplifier 28, the multiplying equalizer 31 and the adder 35, depending on which Hall generators 22 and 23 the multiplexer 27 is actually sampling at that time.

We claim:

1. A device for non-destructive testing of structural faults in a longitudinally displaceable ferromagnetic body comprising:
    means for creating a stationary magnetic field which travels transversely across said body;
    multiple detector means for detecting changes in said stationary magnetic field due to structural faults in said body, said multiple detector means displaced around said body in line with said stationary magnetic field; and
    means for processing said detected changes in said stationary magnetic field to obtain a value of the detected changes, said processing means including displacement compensation means for compensating for detected changes in said stationary magnetic field due to different displacements of said multiple detector means, and
    disproportionate fault compensation means for compensating for the values detected which are of a disproportionate size to actual values of the structural faults which are detected.

2. A device according to claim 1 wherein said processing means includes means for compensating for errors in the multiple detector means which have been amplified by said displacement compensation means and said disproportionate fault compensation means.

3. A device for non-destructive testing of structural faults in a longitudinally displaceable ferromagnetic body comprising:
    a means for creating a stationary magnetic field which travels transversely across said body;
    multiple detector means for detecting changes in said stationary magnetic field due to structural faults in said body, said multiple detector means displaced around said body in line with said stationary magnetic field; and
    means for selecting a detected change from one detector of said multiple detector means;
    a compensation amplifier which has inputs consisting of said detected changes and also of predetermined first compensation values which compensate for displacement of each said detector of said multiple detector means, said compensation amplifier outputting a compensated detected change;
    a multiplying equalizer which has inputs consisting of said compensated detected change and also predetermined multiplication coefficients which compensate for detected changes which are of a disproportionate size to actual values of the structural faults detected, said multiplying equalizer outputting a twice-compensated detected change; and
    an adder which adds said twice-compensated detected changes to predetermined second fault compensation values, said adder outputting the result of this addition.

4. A device according to claim 3, wherein said multiplying equalizer is an analog multiplier which is connected to a register in which multiplication coefficients are stored via an analog-digital converter.

5. A device according to claim 3, wherein said multiplying equalizer is a multiplying analog-digital converter having multiple digital inputs which are connected to a register in which multiplication coefficients are stored.

6. A device according to claim 3, wherein the second fault compensation values are stored in a register.

7. A device according to claim 3 further including:
    registers for said first compensation values, multiplication coefficients and second fault compensation values; and
    a processor which controls said registers and said selection means.

8. A method for producing compensation values and multiplication coefficients comprising the steps of:
    placing a longitudinally displaceable, ferromagnetic, fault-free test sample in a stationary magnetic field which travels transversely across said sample;
    obtaining a measurement from each of a set of magnetic field detectors which are displaced around said test sample in a fixed position and in line with said stationary magnetic field;
    using said measurements to obtain compensation values for each of said magnetic field detectors;
    storing said compensation values in a compensation means;
    placing a longitudinally displaceable ferromagnetic second test sample having known structural defects in said stationary magnetic field;
    obtaining said measurements from each of said magnetic field detectors and compensating said measurements in said compensation means with said compensation values to obtain a compensated measurement;
    using said compensated measurement to obtain multiplication coefficients for each of said magnetic field detectors; and
    storing said multiplication coefficients in a second compensation means.

9. A method according to claim 8, further including the steps of:
    placing a longitudinally displaceable ferromagnetic fault-free test sample in said stationary magnetic field;
    obtaining said compensated measurement from each of said magnetic field detectors and compensating each compensated measurement in said second compensation means to obtain a twice-compensated measurement;
    using said twice-compensated measurement to obtain fault compensation values for each of said magnetic field detectors;
    storing said fault compensation values in a fault compensation means.

* * * * *